United States Patent [19]

Casalnuovo et al.

[11] Patent Number: 5,043,510

[45] Date of Patent: Aug. 27, 1991

[54] AQUEOUS ALKYLATION PROCESS

[75] Inventors: Albert L. Casalnuovo; William A. Nugent, Jr., both of Wilmington, Del.

[73] Assignee: E. I. Du Pont de Nemours and Company, Wilmington, Del.

[21] Appl. No.: 328,881

[22] Filed: Mar. 27, 1989

[51] Int. Cl.$^5$ .............................................. C07C 2/68
[52] U.S. Cl. ................................. 585/466; 585/457; 585/458; 585/469; 585/526; 585/527; 585/605
[58] Field of Search ............... 585/457, 458, 466, 469, 585/605, 526, 527

[56] References Cited

U.S. PATENT DOCUMENTS

| | | | |
|---|---|---|---|
| 3,848,010 | 11/1974 | Intille | 585/457 |
| 4,087,452 | 5/1978 | Kuntz | 260/464 |
| 4,142,060 | 2/1979 | Kuntz | 568/840 |
| 4,594,460 | 6/1986 | Mignani et al. | 568/794 |
| 4,654,176 | 3/1987 | Dang et al. | 260/505 |
| 4,684,750 | 8/1987 | Kessen et al. | 568/883 |

OTHER PUBLICATIONS

Tsuji, Organic Synthesis with Palladium Compounds, (1980).
Okano et al., Chem. Soc. Japan, 1463 (1986), "'Counter' Phase Transfer Catalysis by Water-Soluble Phosphine Complexes".
Kiji et al., Chem. Soc. Japan, 957 (1988), "Palladium-Catalyzed, Atmospheric Pressure Carbonylatine of Allylic Chlorides ...".
Sonogashira et al., Tet. Letters, No. 50, 4467 (1975), "A Convenient Synthesis of Acetylenes: Catalytic Substitution of Acetylenic ...".
Edo et al., Heterocycles, vol. 9, No. 3, 271 (1978), "Coupling Reaction of Monosubstituted Acetylenes with Lodopyrimidines".
Robins et al., J. Org. Chem., vol. 48, No. 11, 1854 (1983), "Nucleic Acid Related Compounds".
Patel et al., J. Org. Chem., vol. 42, No. 24, 3903 (1977), "Palladium-Catalyzed Vinylic Substitution Reactions with ...".
Heck, J. Am. Chem. Soc., 90, 5518 (1968), "Arylation, Methylation, and Carboxyalkylation of Olefins by Group VIII Metal Derivatives".
Mertes et al., J. Am. Chem. Soc., 102, 2033 (1980), "Palladium-Catalyzed Coupling Reactions of Uracil Nucleosides and Nucleotides".
Suzuki et al., Synth. Comm., 11, 513 (1981), "The Palladium-Catalyzed Cross-Coupling Reaction of Phenylboronic Acid ...".
Ishiyama et al., Chemistry Letters, 25 (1987), "Stereoselective Syntheses of Conjugated 1-Phenylthio-1,3-Alkadienes and ...".
Hirao et al., Synthesis, 56 (1981), "A Novel Synthesis of Dialkyl Arenephosphonates".
Xu et al., J. Chem. Soc., Chem. Commun., 1606 (1986), "Stereochemistry at the Phosphorus Atom during Palladium-Catalyzed ...".
Kuntz, Chemtech., 570 (1987), "Homogeneous Catalysis in Water".

*Primary Examiner*—Curtis R. Davis

[57] ABSTRACT

This invention relates to a process for alkylation at carbon and phosphorus sites in an aqueous medium using precious metal catalysts containing sulfonated triarylphosphines (STP) of the generic formula $P(C_6H_4SO_3-)X(C_6H_5)Y$ ($X+Y=3$).

4 Claims, No Drawings

AQUEOUS ALKYLATION PROCESS

BACKGROUND OF THE INVENTION

This invention relates to a process for alkylation at carbon and phosphorus sites in an aqueous medium using precious metal catalysts containing sulfonated triarylphosphines (STP) of the generic formula $P(C_6H_4SO_3^-)_x(C_6H_5)_y (X+Y=3)$.

A review of the use of sulphonated phosphines in homogeneous catalysis is "Homogeneous Catalysis in Water" by Emile G. Kuntz, Chemtech, Sept. 1987, p. 570. Review of the Heck reaction and Pd catalyzed alkylations in non-aqueous media can be found in *J. Organomet. Chem.*, 1989, 360, 409, L. Hegedus; *Organotransition Metal Chemistry: Applications to Organic Synthesis*, Stephen Davies, Vol. 2, 1982, p. 218; *Organic Synthesis with Palladium Compounds*, Jiro Tsuji, 1980.

The use of sulphonated arylphosphines has been reported for unrelated catalytic processes in aqueous media. Hydrocyanation of unsaturated organic compounds utilizing sulphonated triarylphosphines (STP) and Ni or Ni/Pd compounds has been reported (U.S. Pat. No. 4,087,452). Hydroformylation of propene using Rh and STP (U.S. 4,684,750), and telomerization of dienes using STP and Pd has been described (U.S. Pat. No. 4,142,060). The coupling of butadienes to phenols in the presence of Rh complexes and STP has been disclosed (U.S. Pat. No. 4,594,460). Asymmetric hydrogenation, hydroformylation and oligomerization reactions using sulphonated chiral arylphosphines and transition metal compounds has been reported (U.S. Pat. No. 4,654,176). The reduction of allyl chlorides to alkenes using STP, Pd salts and sodium formate has been described (*Chem. Soc. Japan*, 1986, 1463). Allyl chlorides have also been carbonylated to carboxylic acids using STP and Pd salts (*Chem. Soc. Japan*, 1988, 957).

The Pd catalyzed akylatin of aryl or vinyl halides with alkynes, alkenes, and aryl or vinylboronic acids has been extensively reported. Sonogoshira and others have described the alkynylation of aryl and vinyl halides with terminal acetylenes in the presence of Pd triphenylphosphine (TPP) complexes, base and CuI in non-aqueous media (*Tet. Letters*, 1975, 4467; *Heterocycles*, 1978, 9, 271). Robins and others have reported the coupling of iodonucleosides with terminal acetylenes under similar conditions in non-aqueous media (*J. Org. Chem.*, 1983, 48, 1854). Aryl and vinyl halides may also be alkylated by alkenes in the presence of Pd TPP complexes and base in a non-aqueous medium in a reaction commonly known as the Heck reaction (*J. Org. Chem.*, 1977, 42, 3903).

In a variation of the Heck reaction, aryl and vinyl mercurials can be coupled with alkenes utilizing $PdCl_4^{2-}$ (*J. Am. Chem. Soc.*, 1968, 90, 5518). Mertes has reported the coupling of 5-mercurialuridine monophosphates with alkenes in aqueous media using this method (*J. Am. Chem. Soc.*, 1980, 102, 2033).

Suzuki and others have carried out the alkylation of aryl or vinyl halides with aryl or vinyl boronic acids $(RB(OH)_2$ where $R=$aryl, vinyl) utilizing Pd TPP complexes and a base in two phase systems where one phase comprises an aqueous phase (*Synth. Comm.*, 1981, 11, 513; *Chem. Lett.*, 1987, 25). In these systems, the Pd TPP complex and the aryl or vinyl halide are insoluble in the aqueous phase and soluble in the organic phase.

Alkylation at phosphorus has been observed by Hirao and Xu when aryl halides are treated with dialkylphosphites or dialkylphosphine oxides in the presence of base and Pd TPP complexes in non-aqueous media (*Synthesis*, 1981, 56; *J. Chem. Soc., Chem. Commun.*, 1986, 1606).

The above catalysts are to be sure valuable but present significant problems; namely, these catalysts do not operate effectively in an aqueous medium on substrates which are soluble in an aqueous phase and relatively insoluble in an organic phase.

SUMMARY OF THE INVENTION

According to this invention, it has unexpectedly been found that aqueous soluble precious metal catalysts (Group VIII), particularly palladium, platinum, and nickel catalysts, containing arylsulfonated phosphine ligands will catalyze, in the aqueous phase, a variety of alkylation processes, particularly aryl-alkenyl, aryl-alkynyl coupling as well as aryl-aryl coupling. In addition, alkenyl-alkenyl and alkenyl-alkynyl coupling, additionally, aryl or alkenyl phosphorous coupling may take place. The reactions take place under standard alkylation conditions which will be apparent to one skilled in the art. Typically, temperatures will vary between 0°-100° C. and pressures which are, of course, preferred to be ambient may vary between sub-atmospheric to super-atmospheric. Reaction times may vary from a few minutes, e.g. 2 to 4, up to 48 hours. Here again, there is no criticality and proper reaction time will be apparent to one skilled in the art.

DETAILED DESCRIPTION OF THE INVENTION

The present invention provides a catalytic process for preparing arylalkynes, vinylalkynes, biaryls, arylalkenes, alkenylphosphonates or arylphosphonates comprising reacting an aryl halide or vinyl halide having the formula:

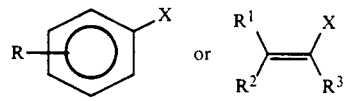

with a compound having the formula:

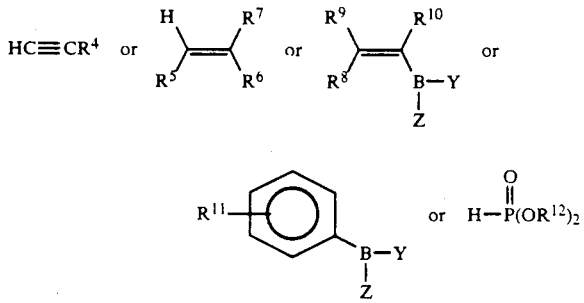

wherein:
R, $R^1$, $R^2$, $R^3$, $R^4$, $R^5$, $R^6$, $R^7$, $R^8$, $R^9$, $R^{10}$, $R^{11}$, and $R^{12}$ are each independently hydrocarbyl, hydrocarboyl, aryl, heteroaryl or heteroalkyl;
X is a halide, preferably bromide or iodide;
Y and Z are OH or are independently selected from groups which are hydrolyzed in water to OH;

under an inert atmosphere in the presence of base and a catalytic amount, preferably 1-20 mol %, of a low-valent Pd complex, wherein:

the Pd complex comprises $Pd(A)_n R^{13}{}_m$ and $Pd(A)_n$, wherein:

A is a sulfonated aryl phosphine ligand moiety;

$R^{13}$ is a phosphine, arsine, or olefin, preferably $C_1$-$C_{20}$ olefin;

n and m are each independently 1 to 4;

provided that when one reactant is $HC\equiv CR^4$, a catalytic amount of a copper (I) salt, such as a copper halide or copper nitrate, is additionally present. R is hydrocarbyl optionally containing heteroatoms The above description can be illustrated by the following equations:

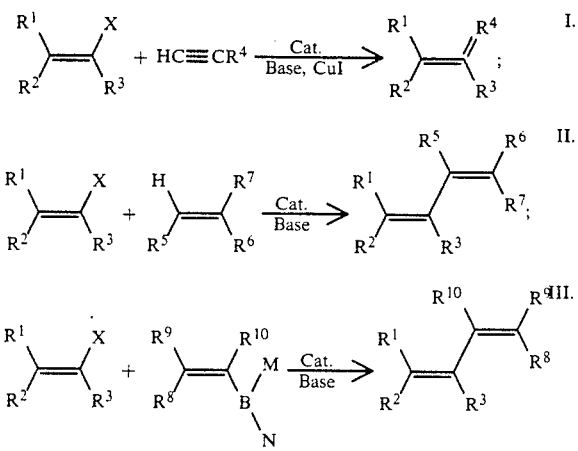

The catalytic process may also be extended to include the reaction of aryl or vinyl halides with dialkylphosphites in aqueous media. This process can be described by the following equation:

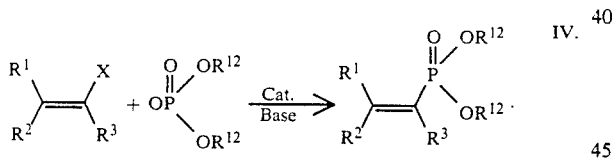

The catalyst employed is a low valent group VIII metal, preferably Pd, complex or precursor containing sulphonated aryl phosphine ligand moieties and may also contain a copper (I) salt as a co-catalyst. The base may be any general base such as trialkylamines, MOH, $M_2CO_3$ or a buffered basic solution. The base should have a pH in water of greater than 8, preferably greater than 10. The solvent system contains water and may contain a co-solvent forming a single phase, such as an alcohol, or may contain an organic co-solvent forming two or more phases.

INDUSTIAL UTILITY

The present invention allows group VIII metal, preferably Pd, catalyzed alkylations to be carried out in an aqueous medium on molecules whose solubility is generally restricted to aqueous solvent systems without the use of protecting groups.

Of particular interest are processes for the preparation of biomolecules such as nucleotides, amino acids, enzymes and DNA. A specific example, shown in Example 1, is the synthesis of the chemically modified uridine nucleotide part of the family of chain terminators used in current DNA sequencing methodology.

Traditional Pd phosphine catalysts employed for alkylations described above are insoluble in water and alcohol and are ineffective in aqueous media when highly hydrophilic substrates such as these biomolecules are used. In addition, alkylations involving hydrophobic substrates can be run in two phase systems, allowing easier separation of catalyst from product.

The illustrations above, Equations I-IV, demonstrate the process of the invention for alkenyl halides. It should be apparent to one skilled in the art that aryl halides or a compound containing an aryl halide moiety can be readily substituted as evidenced by the following examples.

Preparation of Catalyst

The preparation of low valent group VIII complexes containing sulphonated aryl phosphines, including the preparation of sulphonated aryl phosphines, has been described elsewhere (U.S. Pat. No. 4,219,677, U.S. Pat. No. 4,087,452, U.S. Pat. No. 4,483,802). The catalysts employed in the process described herein may be prepared in a similar fashion. In the examples described below, the Pd catalyst employed was synthesized and isolated as a Pd(O) complex using these methods and techniques apparent to one skilled in the art.

EXAMPLES

In the following examples all reactions were run under a nitrogen atmosphere using degassed solvents.

In the following examples, L refers to the sulphonated triarylphosphine ligand $P(C_6H_5)_2(m-C_6H_5SO_3Na)$. In example 1, "dye" refers to a terminal alkyne covalently linked to a fluorescein dye and T-505 refers to the resulting alknylated nucleotide as shown below:

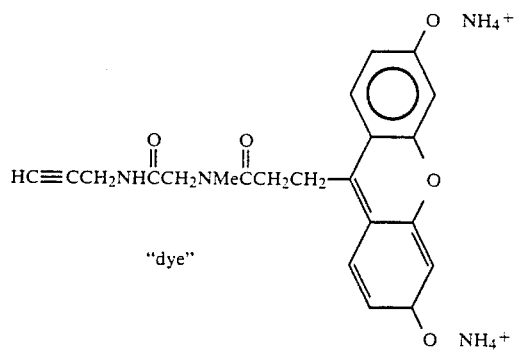

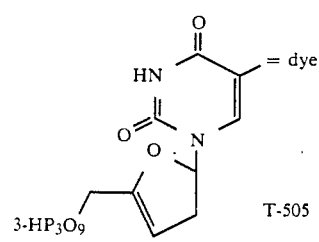

In example 2, the isolated product is the benzofuran derivative shown below. Formation of the benzofuran derivative results from cyclization of the inital alkynylated amino acid.

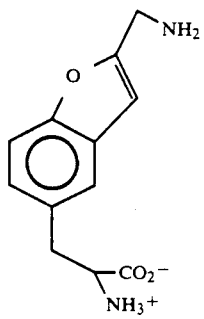

EXAMPLE 1

Synthesis of T-505 Chain Terminator

To a solution of 5-Iododideoxyuridine-5'-triphosphate (100 μmol) and PdL$_4$ (.035 g, 22 μmol) in 3 ml of water was added a solution of the dye (125 μmol), and triethylamine (0.020 g, 200 μmol) in 3 ml of an acetonitrile/water mixture (2:1 v:v). To the resulting bright yellow solution was added dropwise a solution of CuI (0.010 g, 50 μmol) in 1 ml of acetonitrile. The solution was stirred for two hours at 25° C. under N$_2$, the solvent removed in vacuo, and then remaining residue chromatographed (DEAE Sephadex A-25-120 ion exchange column, bead size 40--120 μ) with an aqueous solution of triethylammonium carbonate buffer (pH=7.6, 0.1-1M gradient). The product was collected by U.V. monitoring at 500 nm and then lyaphilized. Yield 47% (by U.V. measurement). The identity of the product was confirmed by comparison to an authentic sample of T-505 and by bioassay as a chain terminating reagent.

EXAMPLE 2

Use of Unprotected Amino Acid

To a solution of iodotyrosine (0.158 g, .5 mmol), PdL$_4$ (0.078 g, 0.05 mmol), triethylamine (0.101 g, 1 mmol) and propargylamine (0.055 g, 1 mmol) in 5 ml of a water/acetonitrile mixture (3:2 v:v) was added dropwise a solution of CuI (0.019 g, 0.1 mmol) in 1 ml of acetonitrile. The resulting dark solution was stirred overnight at 25° C., spiked with phenylalanine as an internal standard and then analyzed by HPLC. The yield was calculated from a standard plot of the pure benzofuran product and phenylalanine. Yield: 82%.

EXAMPLE 3

Use of a Hydrophobic Aryl Iodide and Alkyne

To a solution of p-Iodotoluene (0.109 g, .5 mmol), phenylacetylene (0.102 g, 1 mmol), triethylamine (0.101 g, 1 mmol) and PdL$_4$ (.077 g, .05 mmol) in 8 ml of a water/acetonitrile mixture (3:5 v:v) was added dropwise a solution of CuI (0.009 g, 0.05 mmol) in 1 ml of acetonitrile. The solution was stirred for 3 hours at 25° C. GC analysis using diphenylacetylene as an internal standard indicated a complete consumption of the p-tolyl iodide and a 103% yield of p-tolyphenylacetylene. The identity of the product was confirmed by high resolution GC/MS.

EXAMPLE 4

Use of a Hydrophobic Aryl Iodide and Alkene (Heck reaction)

A mixture of iodotoluene (0.224 g, 1 mmol), ethyl acrylate (0.400 g, 4 mmol), triethylamine (0.202 g, 2 mmol) and PdL$_4$ (0.125 g, 0.08 mmol) in 6 ml of a 50% aqueous acetonitrile mixture was heated at 80° C. overnight. The formation of Pd metal was noted after about 1 hour of heating. GC analysis of the reaction mixture indicated a 63% yield of trans-3 -(p-Tolyl)acrylic acid ethyl ester, 13% yield of toluene and 7% unreacted iodotoluene based on allyl cinnamate as an internal standard. The authenticity of the product was verified by GC/MS and by $^1$H NMR of the isolated product.

EXAMPLE 5

Use of an Iodonucleoside and an Alkenylboronic Acid

A mixture of 5-iododeoxyuridine (0.163 g, .46 mmol), β-phenylethenylboronic acid (0.172 g, 1.17 mmol) and sodium carbonate (0.127 g, 1.20 mmol) were dissolved in 7 ml of a water/ethanol mixture (7:2 v:v). To this solution was added PdL$_4$ (0.050 g, .03 mmol) in 1 ml of water and the reaction mixture then heated at 80° C. for 3 hours. The solution was cooled, filtered, the solvent removed in vacuo and the resulting residue analyzed by $^1$H NMR in CD$_3$OD. Complete consumption of iododeoxyuridine was observed. Two products were observed in the following distribution: trans-5-β-phenylethenyldeoxyuridine 55% and deoxyuridine 45%.

EXAMPLE 6

Biaryl Coupling Using Hydrophilic Arylbromides

To a mixture of sodium p-bromobenzenesulfonate (0.388 g, 1.5 mmol), p-tolyboronic acid (0.136 g, 1 mmol) and PdL$_4$ (0.234 g, .15 mmol) was added 5 ml of water and 2 ml of 1M sodium carbonate. The reaction mixture was heated at 80° C. under N$_2$ for seven hours. The resulting deep brown reaction mixture was cooled and filtered to collect 0.321 g of crude biaryl. The biaryl was washed with benzene, diethyl ether and dried in vacuo to give 0.263 g (97%) of sodium 4-(p-tolyl)benzenesulfonate. $^1$H NMR (CD$_3$OD/D$_2$O, 9:1):2.36, s, 3H, CH$_3$; 7.26, d, 8.0 Hz, 2H, ArH; 7.53, d, 8.1, 2H, ArH; 7.65, d, 8.4, 2H, ArH; 7.85, d, 8.4, 2H, ArH.

What is claimed is:

1. An improved alkylation process wherein an aqueous soluble Group VIII catalyst containing an arylsulfonated phosphine ligand is contacted under catalytic conditions, in the aqueous phase with an aryl or vinyl halide.

2. A catalytic process for preparing arylalkynes, vinylalkynes, biaryls or arylalkenes comprising reacting an aryl halide or vinyl halide having the formula:

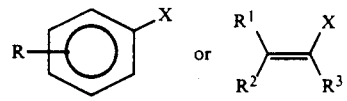

with a compound having the formula:

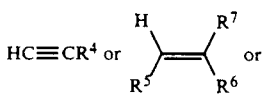

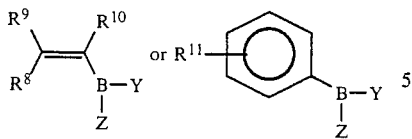

wherein:
R, $R^1$, $R^2$, $R^3$, $R^4$, $R^5$, $R^6$, $R^7$, $R^8$, $R^9$, $R^{10}$ and $R^{11}$ are each independently hydrocarbyl, hydrocarboyl, aryl, heteroaryl or heteroalkyl;
X is a halide;
Y and Z are OH or are independently selected from groups which are hydrolyzed in water to OH;

under an inert atmosphere in the presence of base and a catalytic amount of a low-valent Pd complex, wherein:
the Pd complex comprises $Pd(A)_n R^{13}{}_m$ and $Pd(A)_n$, wherein:
A is sulfonated aryl phosphine ligand moiety;
$R^{13}$ is a phosphine, arsine, or olefin;
n and m are each independently 1 to 4;
provided that when one reactant is $HC\equiv CR^4$, a catalytic amount of a copper (I) salt, such as copper halide or copper nitrate, is additionally present.

3. The process of claim 2 wherein the catalytic amount of palladium is 1–20 mol %.

4. The process of claim 2 wherein the halide is bromide or iodide.

* * * * *